US006450976B2

(12) United States Patent
Korotko et al.

(10) Patent No.: US 6,450,976 B2
(45) Date of Patent: Sep. 17, 2002

(54) APPARATUS FOR MEASURING THE LENGTH AND WIDTH OF BLOOD VESSELS AND OTHER BODY LUMENS

(75) Inventors: Joseph R. Korotko, Troy; Dan Carroll, Ann Arbor; William W. O'Neill, Gross Point Farms; Lisa M. Kurek; Marilyn D. Katz-Pek, both of Ann Arbor, all of MI (US)

(73) Assignee: Accumed Systems, Inc., Ann Arbor, MI (US)

( * ) Notice: Subject to any disclaimer, the term of this patent is extended or adjusted under 35 U.S.C. 154(b) by 0 days.

(21) Appl. No.: 09/803,875

(22) Filed: Mar. 12, 2001

Related U.S. Application Data
(60) Provisional application No. 60/241,118, filed on Oct. 17, 2000, and provisional application No. 60/188,313, filed on Mar. 10, 2000.

(51) Int. Cl.[7] .......................... A61B 5/103; A61B 5/117
(52) U.S. Cl. ........................ 600/587; 600/585; 33/512
(58) Field of Search ...................... 600/587, 591, 600/585, 433, 434, 117, 564, 507; 128/897, 898; 33/501.08, 511, 512

(56) References Cited

U.S. PATENT DOCUMENTS

| | | | |
|---|---|---|---|
| 3,993,045 A | 11/1976 | Ion | 600/481 |
| 4,362,167 A | 12/1982 | Nicolai et al. | 600/591 |
| 4,685,474 A | 8/1987 | Kurz et al. | 600/591 |
| 5,010,892 A | 4/1991 | Colvin et al. | 600/587 |
| 5,239,982 A | 8/1993 | Trauthen | 600/117 |
| 5,253,653 A | 10/1993 | Daigle et al. | 600/585 |
| 5,379,754 A | 1/1995 | Tovey et al. | 600/109 |
| 5,437,290 A | 8/1995 | Bolger et al. | 128/898 |
| 5,471,756 A | 12/1995 | Bolanos et al. | 33/501.45 |
| 5,479,938 A | 1/1996 | Weier | 600/585 |
| 5,657,764 A | 8/1997 | Coulter et al. | 600/591 |
| 5,700,269 A | 12/1997 | Pinchuk et al. | 606/108 |
| 5,702,401 A | 12/1997 | Shaffer | 606/102 |
| 5,709,661 A | * 1/1998 | Van Egmond et al. | 604/117 |
| 5,860,923 A | 1/1999 | Lenker et al. | 600/433 |
| 5,919,147 A | 7/1999 | Jain | 600/587 |
| 6,033,359 A | 3/2000 | Doi | 600/117 |
| 6,078,832 A | * 6/2000 | Lenker et al. | 600/585 |
| 6,319,281 B1 | * 11/2001 | Patel | 623/2.3 |

* cited by examiner

Primary Examiner—Kevin Shaver
Assistant Examiner—Charles Marmor, II
(74) Attorney, Agent, or Firm—Gifford, Krass, Groh, Sprinkle, Anderson & Citkowski, PC

(57) ABSTRACT

Apparatus for measuring length in a blood vessel includes an inner barrel slideably fitting within an outer barrel. The apparatus also preferably includes a zero ring for initializing a position of the inner barrel relative to the outer barrel, wherein the zero ring is rotatably positioned on the outer barrel. The apparatus further includes a small-diameter clamp extending outwardly from the inner barrel for holding a catherization mechanism for visualizing a blood vessel, wherein the catherization mechanism includes a marker and a scale is positioned on the inner barrel for indicating a displacement of the inner barrel relative to the outer barrel in response to the catherization mechanism marker.

10 Claims, 10 Drawing Sheets

APPARATUS FOR MEASURING THE LENGTH AND WIDTH OF BLOOD VESSELS AND OTHER BODY LUMENS

REFERENCE TO RELATED APPLICATION

This application claims priority from U.S. provisional application Serial Nos. 60/188,313, filed Mar. 10, 2000, and 60/241,118, filed Oct. 17, 2000, the entire contents of both being incorporated herein by reference.

FIELD OF THE INVENTION

The present invention relates generally to medical diagnostics and, in particular, to apparatus for measuring length and other physical characteristics of arteries, veins, and other lumens of the body.

BACKGROUND OF THE INVENTION

In the field of medical diagnostics and treatment, cardiologists often treat patients with conditions affecting blood flow in vessels near the heart. In these treatment procedures, various measurements of affected blood vessels need to be accurately determined. In an effort to restore blood flow through cardiac arteries narrowed by plaque deposits or other obstructions, interventional procedures such as balloon catherization, are often used. In this particular procedure, an inflatable balloon is fed into the cardiac artery and inflated to dilate the artery in the affected length of the vessel. After dilation, a stent, which is a thin scaffold or support typically made of plastic or metal and formed in the shape of a perforated tube, is delivered and installed within the blood vessel to maintain an increased blood flow through the cross-sectional flow path.

One of the difficulties cardiologists encounter in this procedure is the measurement of the distance and diameter of the affected length. These measurements are critical, because they are used to determine the stent size appropriate for the length. Accurate sizing of the stent is important to ensure its proper functioning. Consequently, selecting the appropriate stent is critical to the success of the procedure. The prior art contains several methods and apparatuses for making this measurement.

In one prior art approach, a cardiologist reviews x-ray images of the heart after contrast material is introduced into the bloodstream of the patient. The cardiologist must rely on experience and training to make a judgment regarding the size of the affected length. As such, this method may not always provide repeatability and precision in the measurement of the length.

In another prior art approach, x-ray images are processed by computer image analysis systems, which estimates the dimensions of the affected length. These measurements are based on various assumptions about the position of the artery, the axis of the x-ray image, etc. Also, the additional equipment required for this procedure may make it economically unfavorable or even cost-prohibitive. A further prior art approach uses ultrasonic transducers that are fed into the patient's arteries via a catheter which "images" the vessel walls to estimate the length. This device is also very expensive and cumbersome to use.

In view of the foregoing, there is a need in the art to provide a new, simple device capable of accurately measuring the dimensions of a length, within a blood vessel, such as a cardiac artery.

SUMMARY OF THE INVENTION

The present invention is directed to devices for measuring length and/or diameter in arteries, veins, and other lumens of the body. In a length-measuring embodiment, the apparatus includes a hand-held unit which remains outside the body, but which couples to, and cooperates with, one or more invasive catheters and/or guidewires to measure a length within a vessel. The hand-held unit further includes an inner barrel and outer barrel that slide relative to one another to position a scale with markings indicative of the length. The preferred embodiment also includes a zero ring for initializing the relative position of the barrels and scale in conjunction with the onset of the length measurement to ensure the accuracy of a measurement. The apparatus optionally includes a feature to hold a guidewire in a stationary position.

As is typical in the surgical profession, a radio opaque marker or similar device is placed on the catheter tip or other distal point. The marker point is then positioned at one end of the lesion, and subsequently displaced to the opposite end of the lesion using the inventive device. The measurement of a lesion, plaque region, obstruction, or other length of interest may be made by using the device according to the present invention.

One advantage of the invention is that the device may be used to measure the distance between any two points in the blood vessel. Another advantage is that the device may be used for measurement in any vessel that it or an attached catheter and/or guidewire can be inserted into and that fluoroscopy can view. A further advantage of the present invention is that the apparatus is used in a variety of manners to determine the dimensions of a length of the blood vessel.

A device for measuring the inside diameter of a vessel according to the invention includes a tube, measuring wires, and a knob. The tube is as long as necessary to reach the desired location, yet flexible enough to maneuver through vasculature. Holes run the length of the tube to accommodate multiple lumens including a central lumen that runs the entire length of the tube and a plurality of other lumens which are uniformly spaced around the central lumen but stop a short distance from the tip of the tube. These other lumens also have a slot cut into them that exposes a portion of the lumen. Wires are inserted in all the lumens except the central lumen. When the wires are pushed on their proximal ends, they expand by bulging out of the slots into the respective lumens. When the wires make contact with the inside of the vessel, they indicate the inside diameter of that vessel.

DETAILED DESCRIPTION OF THE PREFERRED EMBODIMENT

Figure 1:
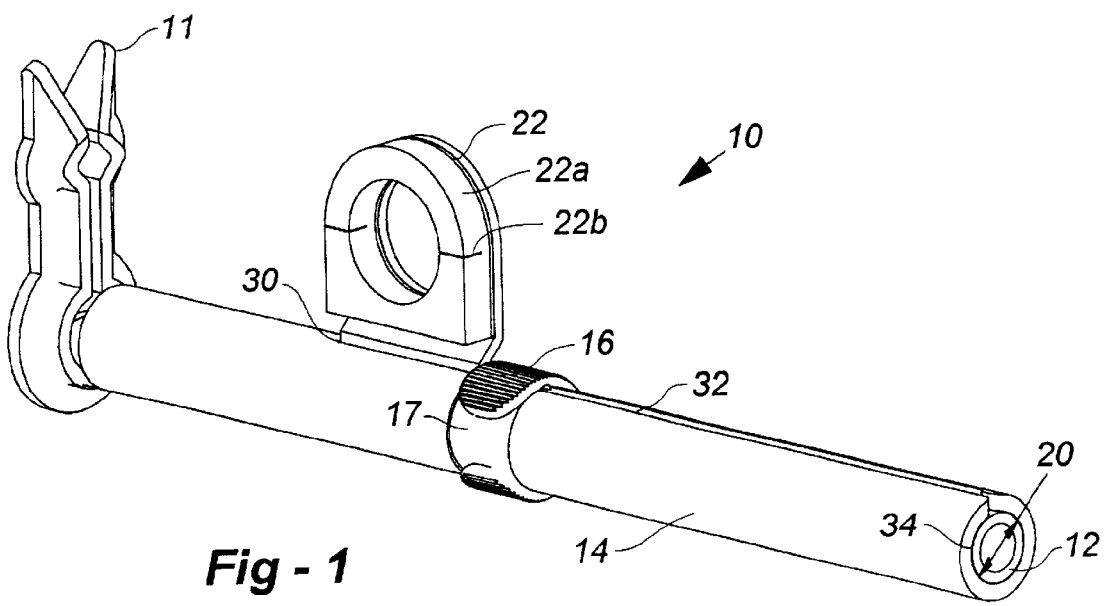
FIG. 1 is a perspective view of preferred apparatus in the zero position according to the invention for measuring length in a blood vessel.

FIGS. 1 through 6 depict a preferred embodiment according to the invention for measuring length in a blood vessel. The apparatus 10 includes two main components, an inner barrel 12 and an outer barrel 14. The inner barrel 12 is an elongate member having a cross-sectional diameter of sufficient size to allow the inner barrel 12 to slide within the inner diameter 20 of the outer barrel 14. Hence, the length measuring apparatus 10 of the present invention can be referred to as a telescoping device. All components of the length measuring device 10 can be made from a variety of materials though preferably medical-grade plastic is used, where possible.

Figure 5:
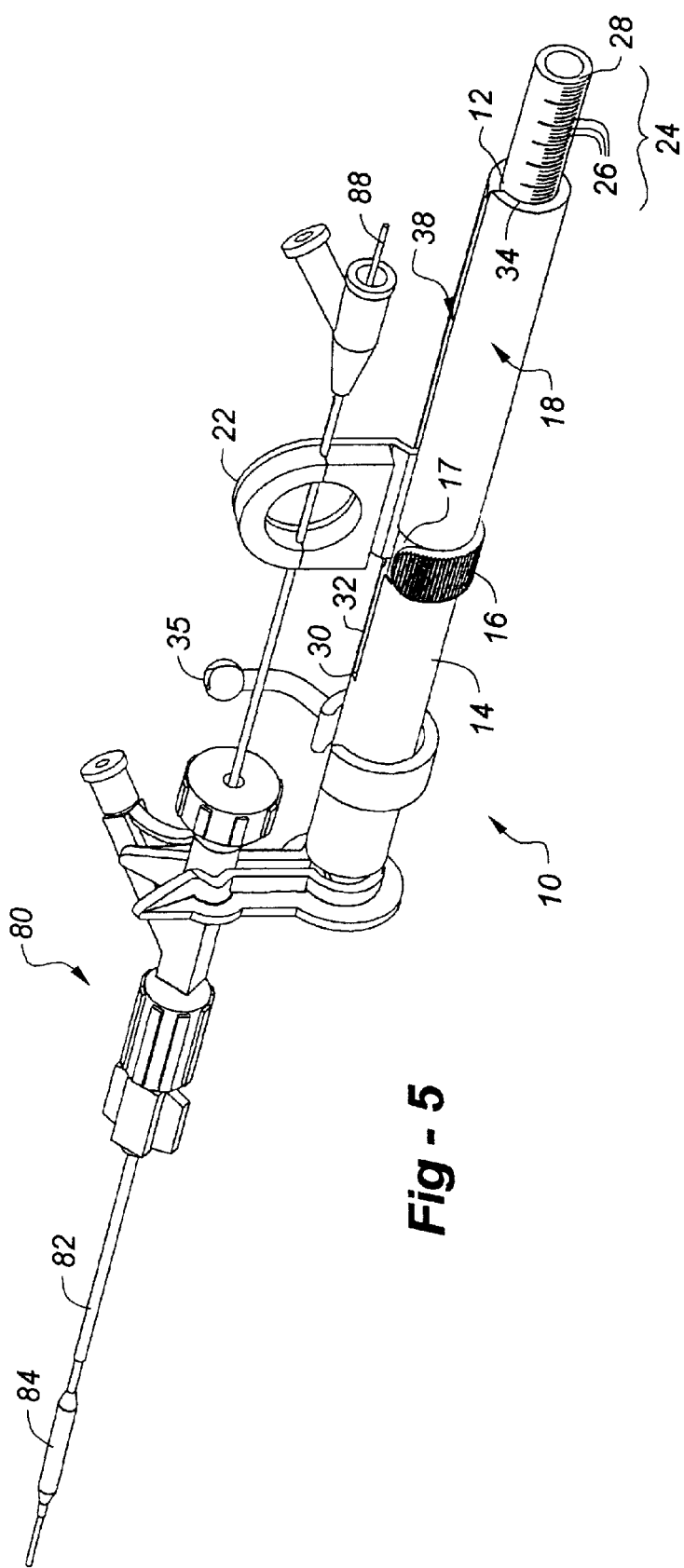
FIG. 5 is a perspective view of the preferred apparatus of FIG. 1 coupled to a catherization assembly.
Figure 6:
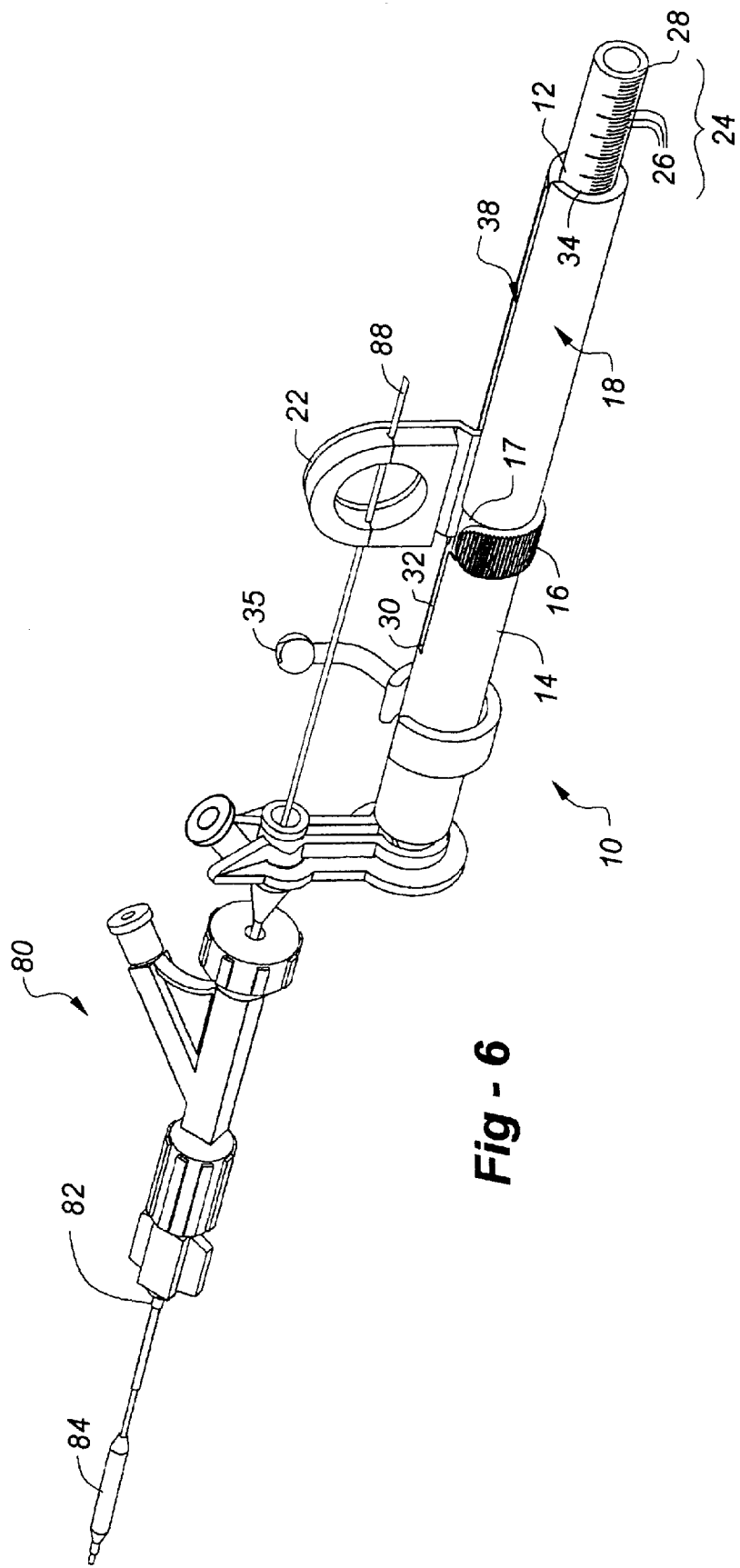
FIG. 6 is a perspective view showing an alternative coupling to a catherization assembly.

The inner barrel 12 extends to a small-diameter clamp 22 comprising a pad of resilient material 22a having a slit 22b. This configuration allows the slit 22b to receive and retain smaller-diameter elements such as catheters or guidewires of various diameters through a simple insertion into the slit 22b of the pad 22a. In one mode of operation, the shaft of a balloon catheter is pushed into the slit 22b, as shown in FIG. 5. Alternatively, a guidewire may be received by the slit, as shown in FIG. 6. The pad 22a may be composed of any resilient material capable of reliably retaining these smaller-diameter elements, preferably without slippage. For example, dense foams and rubber-like materials may advantageously be used for such purpose.

Figure 2:
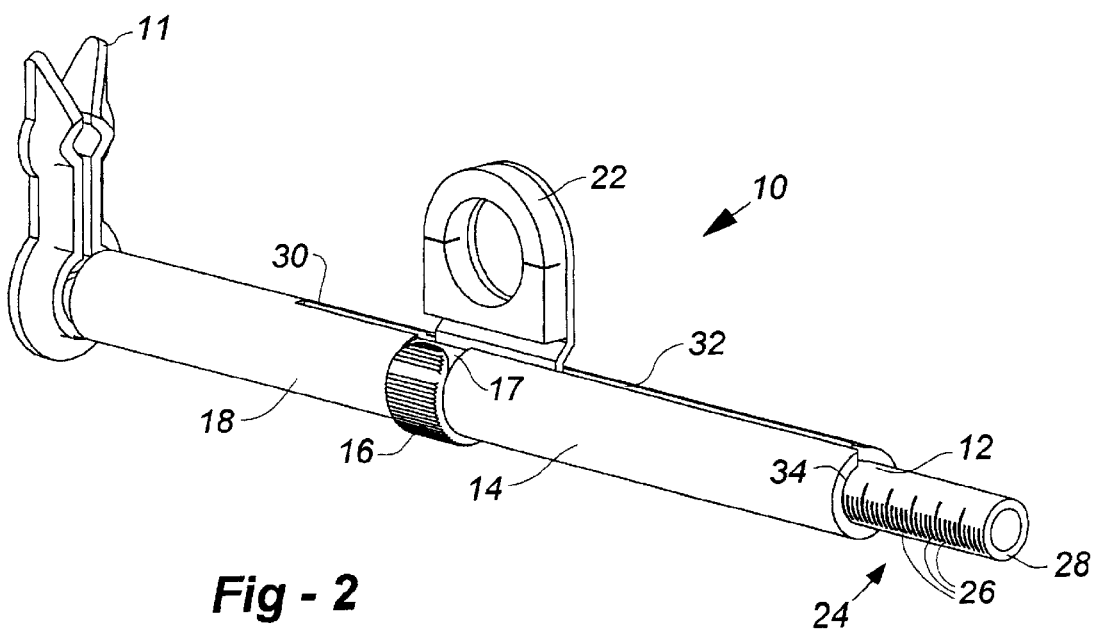
FIG. 2 is a perspective view of the apparatus of FIG. 1 showing the inner barrel displaced along the length of the outer barrel.
Figure 4:
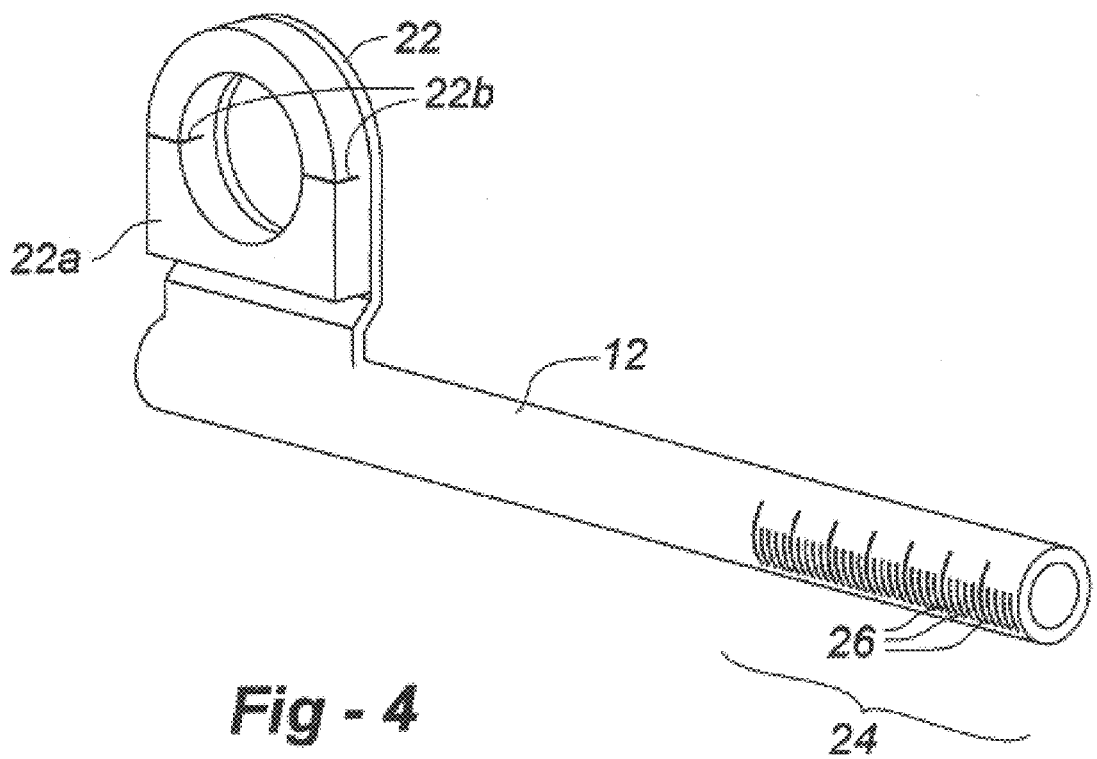
FIG. 4 is a perspective view of an inner barrel associated to the apparatus of FIG. 1.

Referring to FIGS. 2 and 4, the apparatus 10 includes a scale 24 marked on the inner barrel 12. The scale 24 serves as a visual reference representing the displacement that occurs during a measurement. The scale 24 contains graduations 26 marked off in units of distance or size. The scale 24 preferably further includes a zero mark 28 that corresponds to zero displacement of the inner barrel 12. When the small-diameter clamp 22 of the inner barrel 12 is seated in the terminus 30 of the main slot 32 of the outer barrel 14, the scale 24 is in the zero position. That is, the zero mark 28 of the scale 24 is in line with the edge 34 of the main opening 21 of the outer barrel 14. In this position, no displacement of the inner barrel 12 has occurred.

When the inner barrel 12 is displaced within the outer barrel 14, the scale 24 is exposed as the inner barrel 12 leaves the main opening 21 of the outer barrel 14. The distance of the displacement of the inner barrel 12 is indicated on the scale 24. A reading of the distance is taken by determining the point at which the edge 34 of the main opening 21 of the outer barrel 14 aligns with the scale 24. Alternatively, a pointer or other indicator may be attached to or defined by the outer barrel 14 and used to indicate the displacement distance on the scale 24.

The outer barrel 14 is an elongate member that defines a main slot 32 for accommodating the small-diameter clamp extension of the inner barrel 12, while preventing rotational movement of the inner barrel 12 within the outer barrel 14. The main slot 32 preferably extends from the main opening 21 of the outer barrel 14 to a terminus 30 at the opposite end of the outer barrel 14, but does not extend completely to the opposite end of the outer barrel 14.

The outer barrel 14 further defines a guidewire hook 35, shown in FIGS. 5 and 6. The guidewire hook 35 is an outwardly extending projection, or projections, that extend away from the body of the outer barrel 14. Preferably, the guidewire hook 35 clips to the outer barrel 14, enabling the guidewire hook 35 to be located at any position along the length of the outer barrel. Alternatively, the guidewire hook 35 can be integrally formed in or attached to the outer barrel 14. In any case, the guidewire hook 35 is fashioned in a manner so as to allow it to receive a guidewire during a measurement procedure and retain the guidewire in a stationary position until measurement is complete. This allows a user to perform a measurement without moving the guidewire, which can be critical when using the length measuring apparatus 10 in conjunction with certain catheter systems, such as those using a rail system design, as is known in the art.

Figure 3:
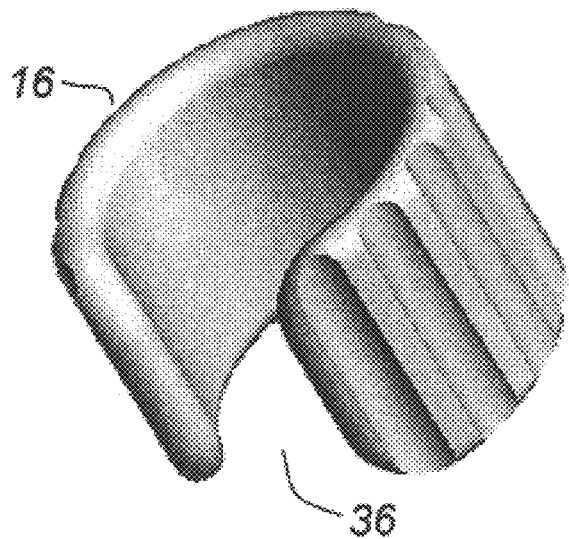
FIG. 3 is a perspective view of a zero ring according to the invention.

Referring to FIG. 3, the apparatus 10 includes a zero ring 16, such as a ring- or band-like member, that sits in a recess 17 in the outer surface 18 of the outer barrel 14. Preferably, the zero ring 16 fits over the outer barrel 14 in a snap fashion. That is, the outer barrel 14 is pressed through the slot 36 of the zero ring 16 until the zero ring 16 snaps around the outer surface 18 of the outer barrel 14. A portion of the zero ring 16 is cut away, creating a slot 36, to give the zero ring 16 a "C"-shaped configuration.

The width of the slot 36 on the zero ring 16 is sufficient to allow the extension of the inner barrel 12 including the small-diameter clamp to pass through the slot 36 without excessive resistance. The inner diameter of the zero ring 16 is large enough to allow the zero ring 16 to rotate about the outer surface 18 of the outer barrel 14 with only slight friction. This allows the zero ring 16 to remain in a selected position relative to the outer barrel 14 following rotation. Also, the inner diameter of the zero ring 16 is small enough to prevent the zero ring 16 from being easily removed from the outer barrel 14.

The zero ring 16 operatively retains the inner barrel 12 in the zero position. Accordingly, the zero ring 16 can take on any form appropriate for this retention function. For example, the zero ring 16 may include a pin that passes through holes of the inner 12 and outer 14 barrels when aligned properly, a latch that retains the inner barrel within the outer barrel, a clamp that compresses the inner 12 and outer 14 barrels together, or any other form and/or structure capable of achieving the retention function.

As shown in FIGS. 5 and 6, the apparatus of the invention may be used with any commercially available catheterization assembly 80, such as a guide catheter, balloon catheter, and so forth. For example, during a typical angioplasty procedure, a guide catheter 82 is inserted into the ostium (not shown) of either the left or right main coronary artery (not shown). A balloon catheter 84 is then inserted through the guide catheter and advanced to the location of the lesion (not shown). The balloon is inflated to dilate the vessel. It is at this time that a medical professional determines length of the lesion. The length measurement apparatus 10 is clamped onto the side of the guide catheter and balloon catheter. The small-diameter clamp 22 can receive and retain the balloon catheter, as shown in FIG. 5, or a guidewire itself 88, as shown in FIG. 6. Preferably, the guidewire hook 35 is utilized with rail-type system catheters. In this type of catheter assembly, the balloon catheter and guidewire are positioned side-by-side. Thus, the balloon catheter may be received within the slit of the small-diameter clamp 22, with the guidewire being placed within the guidewire hook 35.

The zero ring 16 controls the displacement of the inner barrel 12 of the length measuring device 10. When displacement of the inner barrel 12 is not desired, such as during attachment of the length measuring apparatus 10 to a catheterization assembly, the zero ring 16 is rotated about the outer surface 18 of the outer barrel 14 to a closed position, i.e., a point where the slot 36 of the zero ring 16 is not aligned with the main slot 32 of the outer barrel 14. In this configuration, the small-diameter clamp 22 of the inner barrel 12 remains seated in the terminus 30 of the main slot 32 and is physically prevented from moving out of that position. In this configuration, the scale 24 remains in the zero position, indicating that no displacement has occurred. When displacement is desirable, such as during a measurement procedure, the zero ring 16 is rotated about the outer surface 18 of the outer barrel 14 to an open position, i.e., a point at which the slot 36 of the zero ring 16 is aligned with the main slot 32 of the outer barrel 14. In this position, an open passageway 38 is defined by the slot 36 of the zero ring 16 and the main slot 32 of the outer barrel 14. The small-diameter clamp 22 of the inner barrel 12 can travel through this open passageway 38, thereby allowing the inner barrel 12 to be displaced along the length of the outer barrel 14.

The length measuring apparatus 10 may be utilized in conjunction with a catheterization assembly having two catheters, or one catheter and one guidewire. The catheters and/or guidewires contain a radio-opaque marker that marks the ends of the length of interest in the blood vessel. In operation, the length measuring apparatus 10 is attached either to the two catheters, or to the one catheter and one guidewire. Note that the large-diameter hub clamp 11 may be clamped onto either the hub of a guide catheter, a y-connector, a hub of a balloon catheter, or another type of hub, as is known in the art. This is accomplished by forcing the hub into the hub clamp 11. The hub clamp 11 is an upstanding projection or projections on the outer barrel 14. The hub clamp 11 has various structural features that allow it to receive and retain hubs and other bodies of various sizes and configurations.

Next, the shaft of the balloon catheter or guidewire is pressed into the slit 22b of small-diameter clamp 22. If a rail system catheter is used, the guidewire is secured to the outer barrel 14 by pressing the guidewire into the guidewire hook 35. During this attachment process, any displacement of the inner barrel 12 may expose a portion of the scale 24 and, consequently, could affect a subsequent measurement. To prevent this, the zero ring 16 is rotated to the closed position, which prevents such displacement by retaining the small-diameter clamp 22 of the inner barrel 12 in the terminus 30 of the main slot 32 of the outer barrel 14. In this configuration, the length measuring device 10 is attached to the catheter(s) and/or guidewires without disturbing the position of the inner barrel 12. Furthermore, the zero ring 16 prevents displacement during any positioning of the markers conducted subsequent to the attachment process.

Once the length measuring device 10 is attached to the catheter(s) and/or guidewires, the operator performs the measurement. The zero ring 16 is rotated to the open position, i.e., aligning the slot 36 of the zero ring 16 with the main slot 32 of the outer barrel 14. An open passageway 38 is formed that allows inner barrel 12 to move out of the terminus 30 of the main slot 32 of the outer barrel 14. Next, the inner barrel 12 and the attached catheter or guidewire are slideably displaced along the length of the outer barrel 14. During this step, the small-diameter clamp extension 22 travels along the open passageway 38 and the scale 24 is gradually exposed. The inner barrel 12 is displaced until the end of the length of the blood vessel being measured is reached. Once the desired position is reached, the operator obtains the length measurement by reading the last exposed graduation 26 on the scale 24, i.e., the graduation 26 aligned or nearly aligned with the main edge 34 of the main opening 21, or an attached or integral pointer or other indicator, if present, of the outer barrel 14.

The length measurement apparatus 10 functions with a catheterization mechanism 80 such as an over-the-wire catheter system or a rail system, as is known in the art. Also, the length measuring apparatus 10 may include a component that allows it to serve as the sole apparatus used in the measurement of a length of the blood vessel. For example, the inner and outer barrels may comprise elongate catheters having a marker such as a radio-opaque marker, fixed on a terminal end. In this example, no catheter or guidewire separate from the length measuring apparatus need be utilized to obtain a measurement of the length. A measurement with this embodiment would be determined in the same manner detailed above, i.e., the displacement distance would be determined by reading the scale.

As can be readily understood by persons of ordinary skill in the art, the length measurement apparatus 10 may include other suitable devices, components, accessories and combinations.

Figure 7:
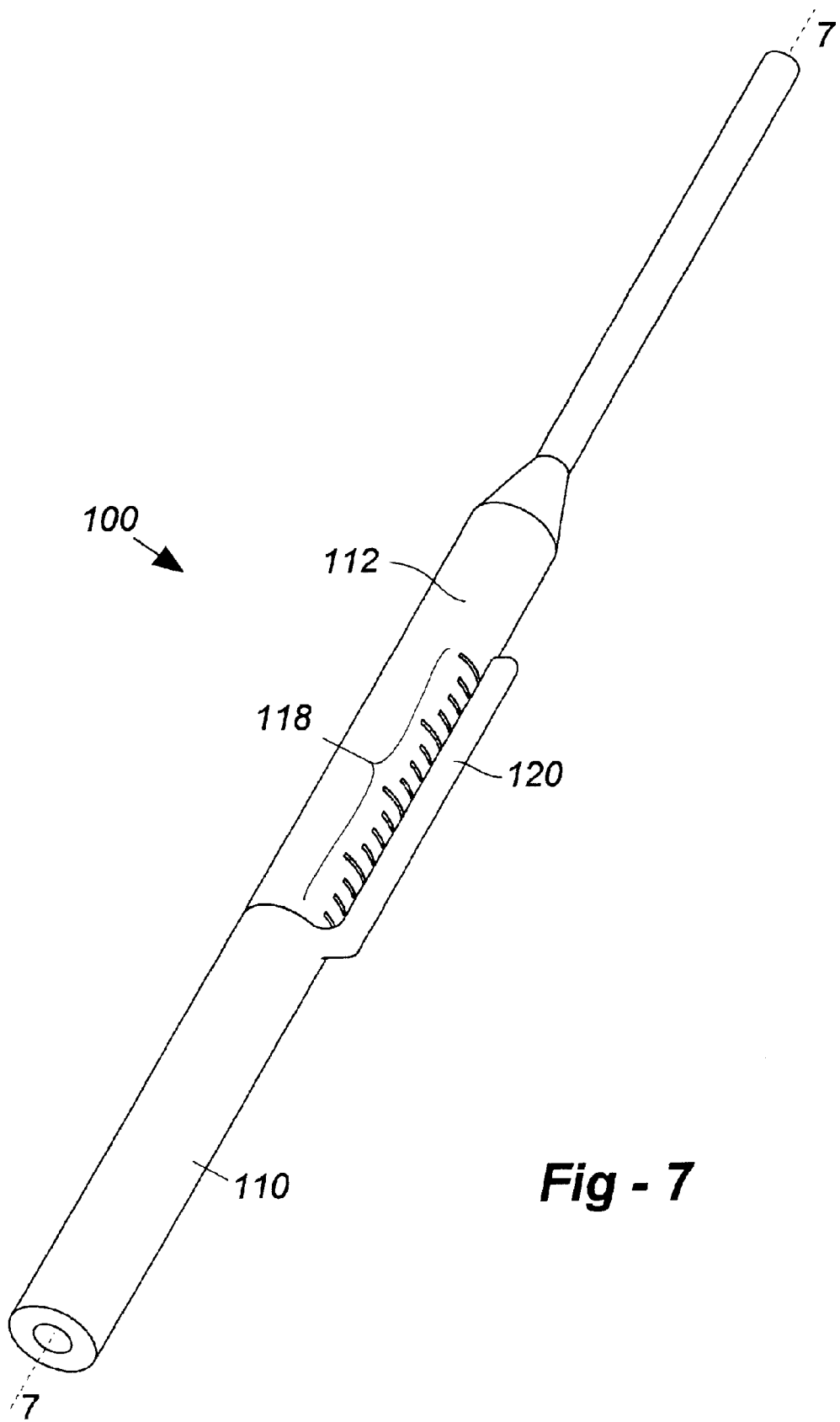
FIG. 7 is a plan view of an alternative embodiment of the invention having a dual marker.
Figure 8:
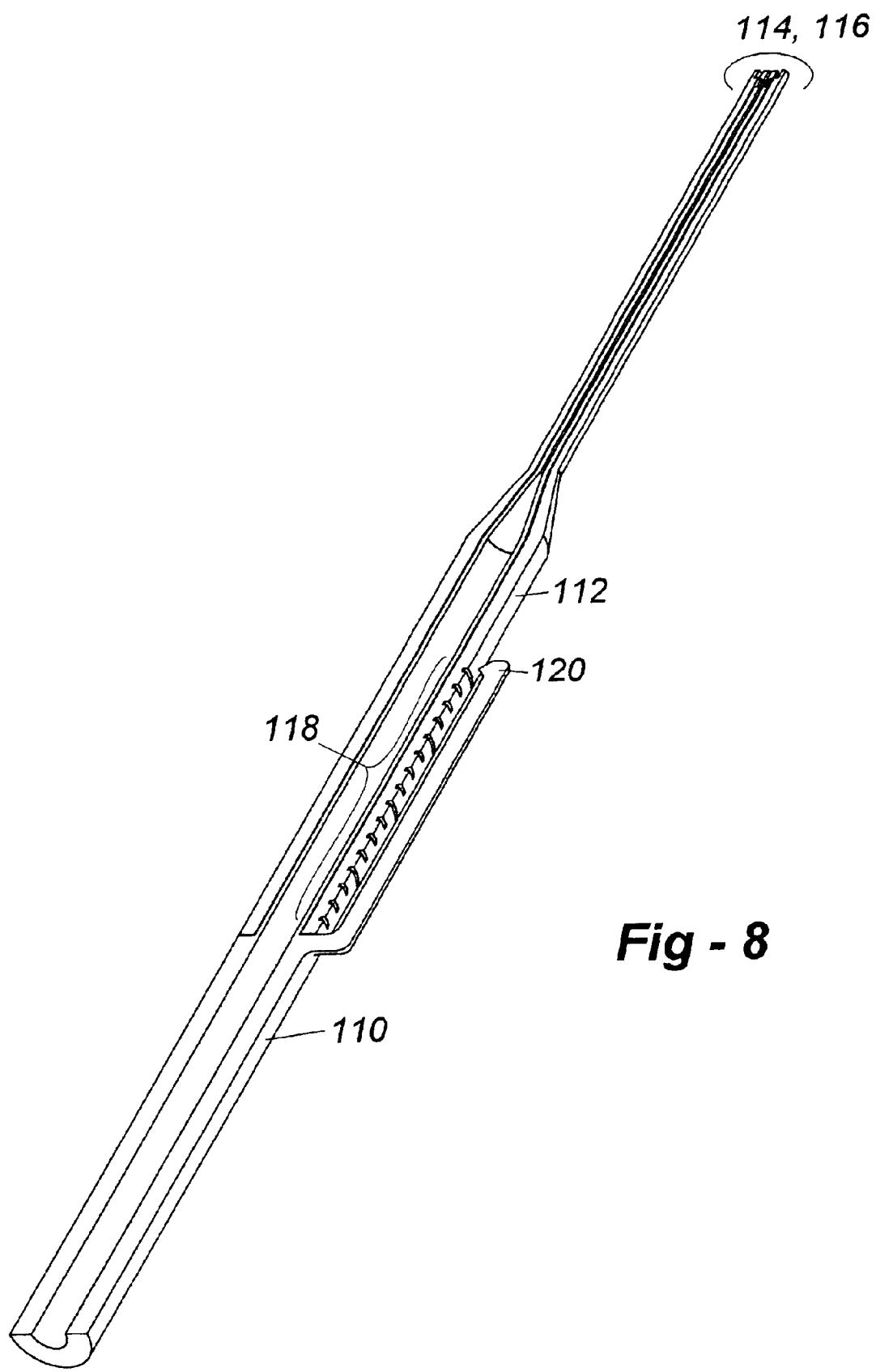
FIG. 8 is a sectional view taken along line 7—7 of FIG. 7 with the markers together.

Referring to FIG. 7, another embodiment of an apparatus 100 for measuring length in a blood vessel is illustrated. The apparatus 100 utilizes a caliper with two main components, an inner barrel 110 and an outer barrel 112. The inner barrel 110 and outer barrel 112 are in a closed position. The inner barrel 110 is small enough to slide along the inside of the outer barrel 112. As seen in FIG. 8, a marker such as a radio-opaque marker 114, 116 is embedded in the tip of each barrel 110, 112. On the other end of the barrels are hubs 110, 112. The outer barrel hub 112 has a scale 118 on it and the inner barrel hub 10 has an indicator 120. The hubs 110, 112 are designed so that the indicator 120 and scale 118 work together.

When the caliper is in a "closed" position, the radio-opaque markers 114, 116 of both barrels 110, 112 are flush to each other and the hubs 110, 112 are flush to each other. Also, the indicator 120 is pointing to the zero mark on the scale 118 in this position. As the barrels 110, 112 are pulled apart, the markers 114, 116 and the hubs 110, 112 separate. The indicator 120 and scale 118 show how far apart the barrels 110, 112 have been pulled. The barrels 110, 112 are pulled apart to the desired position in order to make the measurement. The radio-opaque markers 114, 116 are visible by fluoroscopy, thus allowing the physician to pull the barrels 110, 112 apart to the correct distance. For example, one marker 116 would be positioned at the proximal (near) end of the lesion and the other marker 114 would be at the distal (far) end. The barrels 110, 112 are flexible so that they can be inserted into the vascular system to the desired location. The inner barrel 110 may also be cannulated so that it can placed over a guidewire to facilitate insertion. Preferably, the diameter of the barrels 110, 112 are small enough to be inserted into the lumen of the artery or lesion.

Figure 9:
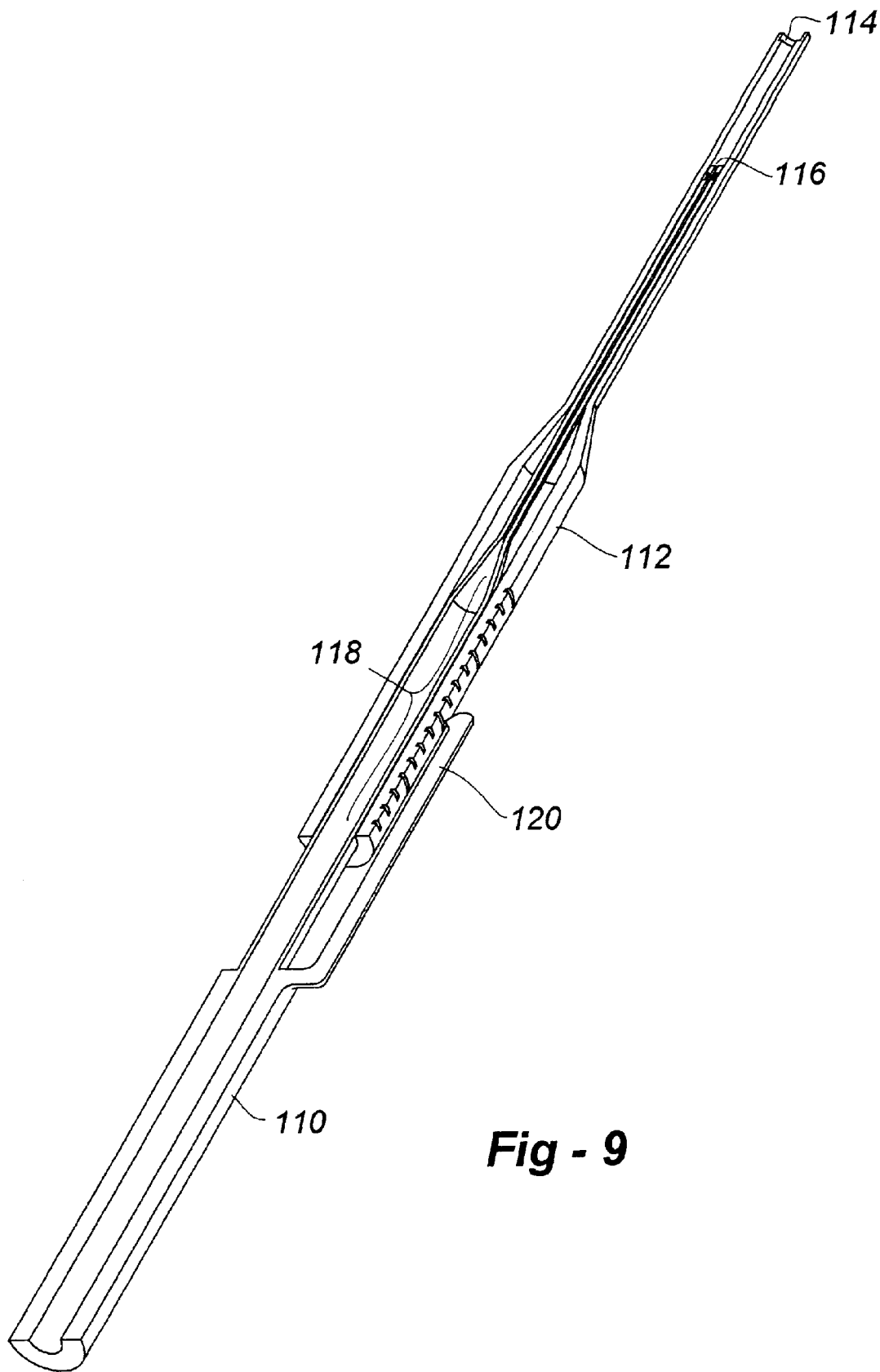
FIG. 9 is a sectional view taken along line 7—7 of FIG. 7 with the markers separated.

FIG. 8 is a sectional view of FIG. 7 illustrating the fit of the barrels 110, 112, the flushness of the radio-opaque markers 114, 116, and the indicator 120 pointing to zero on the scale 118. FIG. 9 is another sectional view of FIG. 7 illustrating the barrels 110 and 112 pulled apart. The indicator 120 and scale 118 show how far the markers 114 and 116 have been pulled apart. In this example, the barrels 110, 112 are relatively short. One skilled in the art will be appreciated that the barrels 110, 112 are long enough to reach the desired locations.

In this example, the method of showing the measurement is through the use of an indicator 120 and scale 118, however other methods are possible. As the barrels 110, 112 are pulled apart, a hub drives a mechanical means for showing the measurement on a counter or a needle deflected scale. Alternatively, an electronic means is utilized to measure the distance between the markers 114, 116.

Figure 10:
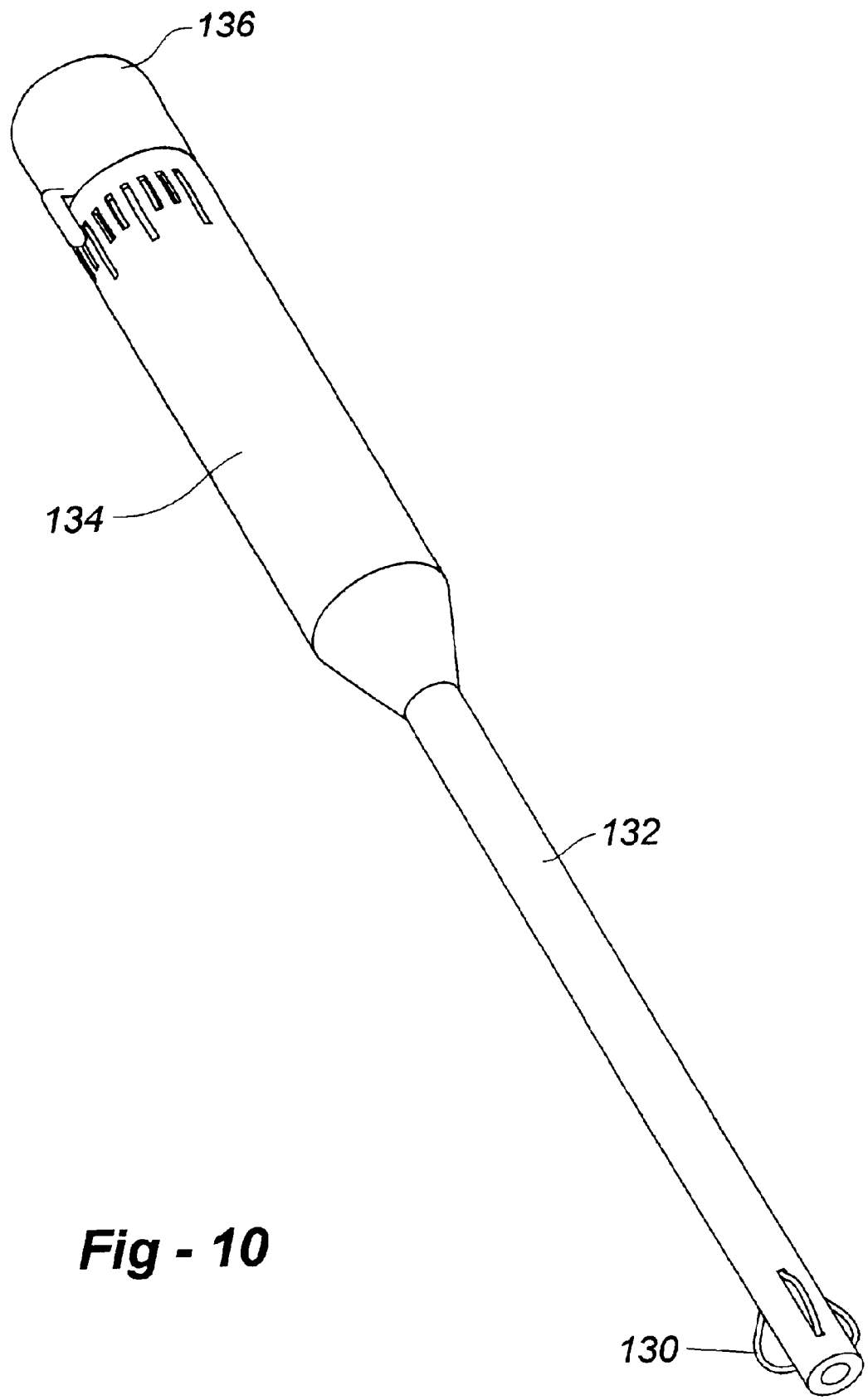
FIG. 10 is a perspective view of still another embodiment of the invention having a rotating as opposed to translational indicator.

Referring to FIG. 10, a device for measuring the inside diameter of a vessel illustrated. The device has a tube 132, measuring wires 130, and a knob 136. The tube 132 is long and flexible. Its length is as long as necessary to reach the desired location, for example long enough to reach the coronary arteries from a transfemoral approach. The tube 132 is also flexible enough to maneuver through vasculature. Holes run the length of the tube 132 so that it has multiple lumens.

Figure 11:
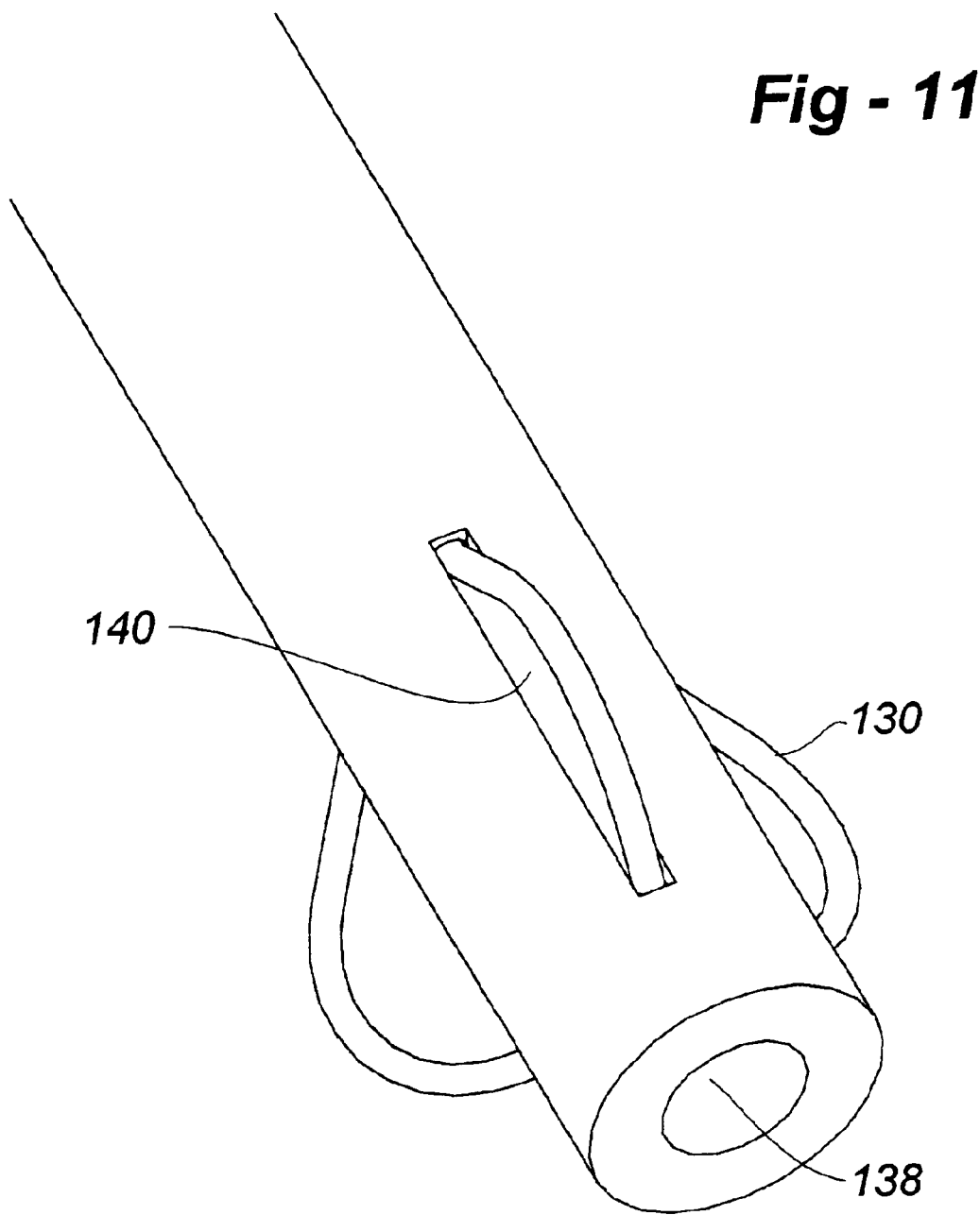
FIG. 11 is an enlarged perspective view of the tip end of the apparatus of FIG. 10.

Referring to FIG. 11, a central lumen 138 running the entire length of the tube 132 is illustrated. The other lumens are uniformly spaced around the central lumen 138 and do not run the length of the entire tube 132. They stop a short distance from the tip of the tube 132. These lumens also have a slot cut into them that exposes a portion of the lumen. Wires 130 are inserted in all the lumens of the tube 132 except the central lumen 138. These are measuring wires 130 that will expand to indicate the inside diameter of the vessel. When these wires 130 are pushed on one end, they will expand by bulging out of the tube 132 through the slots 140 cut into the lumen. When the wires 130 make contact with the inside of the vessel, they indicate the inside diameter of that vessel.

Figure 12:
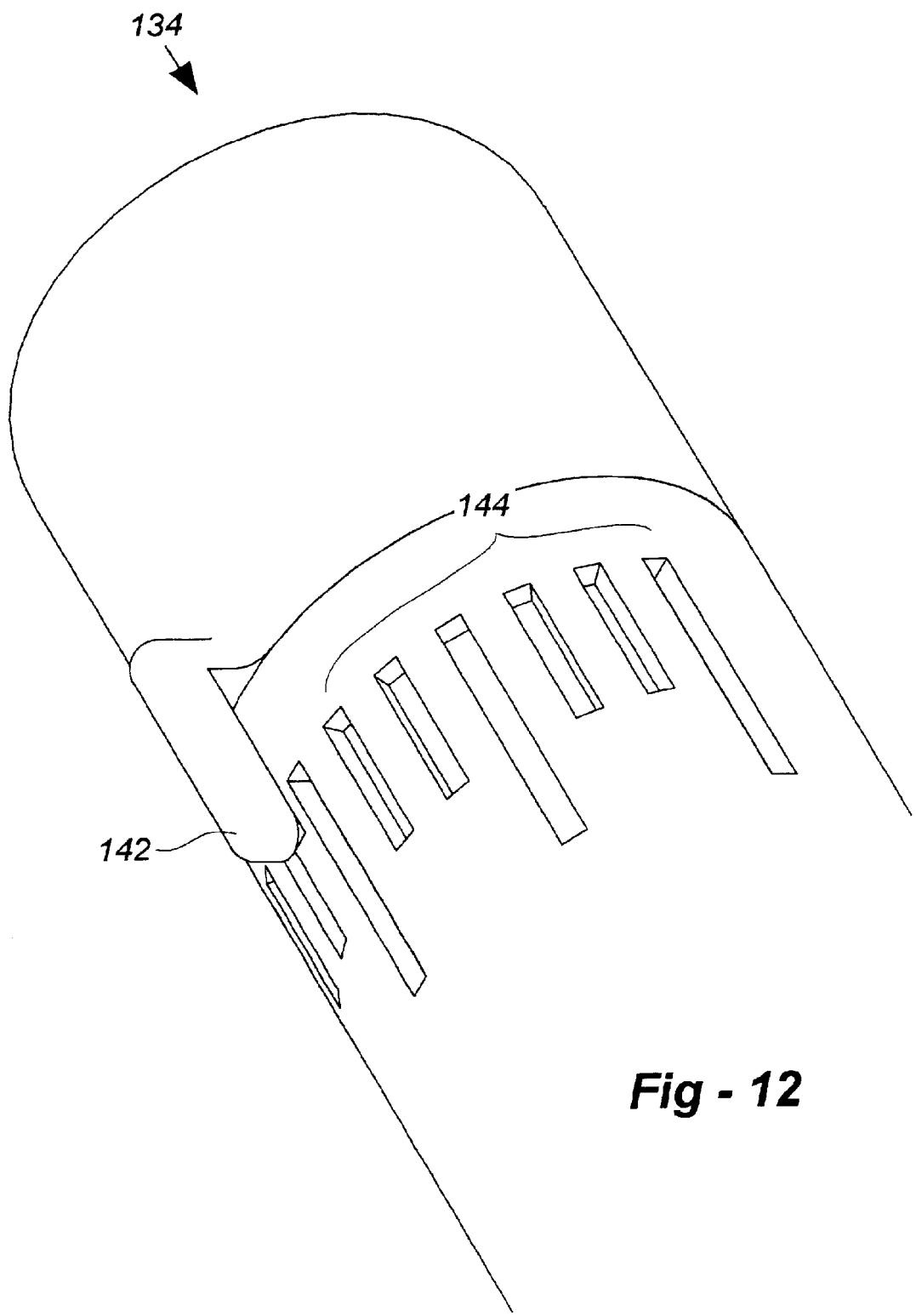
FIG. 12 is an enlarged perspective view of the knob end of the apparatus of FIG. 10.

The proximal end of handle 134 is illustrated in FIG. 12. The handle 134 can be pushed, pulled, twisted, or turned in order to get the tip of the tube 132 to the correct location. The handle 134 also has a knob 136 built into it. The knob 136 is used to push on the wires 130 as described above. When the knob 136 is turned, it pushes on the end of the wires 130 and they bulge out. The handle 134 also has a scale 144 and pointer 142. The scale 144 is on one part of the handle 134 and the pointer 142 is on the knob 136, or vice versa. When the knob 136 is turned so that the pointer 142 indicates zero on the scale 144, the measuring wires 130 do not bulge out of the tube 132. As the knob 136 is turned, the wires 130 bulge. The knob 136 will be turned until the wires 130 touch the vessel. At this time, the pointer 142 will indicate the size of the diameter on the scale 144.

This device can be used to measure the inside diameter of a vessel or even the inside diameter of a stent after it has been expanded. It has the advantage of being a convenient, fast, simple, easy, and accurate way to measure diameter. Its probable use is for the inside of vessels, arteries, veins, or other lumens of the body.

We claim:

1. Apparatus for measuring length in a body lumen in conjunction with a catherization assembly having a larger-diameter stationary component and a smaller-diameter moveable component with at least a distal end of the moveable component terminating in a radio-opaque marker, the apparatus comprising:

an outer barrel including a large-diameter clamp adapted for retaining the larger-diameter stationary component of the catherization assembly;

an inner barrel, slideably disposed within the outer barrel, the inner barrel including a small-diameter clamp adapted for retaining the smaller-diameter moveable component of the catherization assembly; and a scale operative to show a relative position of the inner barrel with respect to the outer barrel, thereby indicating the relative position of the moveable component within the body lumen.

2. The apparatus of claim 1, wherein:

the catherization assembly includes a guide catheter and a catheter having a radio-opaque marker;

the large-diameter clamp retains the guide catheter; and the small-diameter clamp retains the catheter having the radio-opaque marker.

3. The apparatus of claim 1, wherein:

the catherization assembly includes a catheter and a guidewire;

the large-diameter clamp retains the catheter; and the small-diameter clamp retains the guidewire.

4. The apparatus of claim 1, further including a zero position wherein a position of the inner barrel is fixed relative to the outer barrel, enabling the catherization assembly to move as a unit to achieve an initial position within the body lumen.

5. The apparatus of claim 1, wherein the outer barrel is an elongated member having a cross-sectional diameter allowing the inner barrel to slide therewithin.

6. The apparatus of claim 1, wherein the outer barrel includes a slot through which the small-diameter clamp extends.

7. An apparatus of claim 1, wherein the outer barrel includes a guidewire hook.

8. The apparatus of claim 1, further including a zero ring disposed within a recess in the outer barrel for operatively retaining said inner barrel in an initial position.

9. The apparatus of claim 1, wherein both the larger-diameter stationary component and smaller diameter moveable component terminate in distal ends with radio opaque markers.

10. The apparatus of claim 2, wherein the catheter having the radio-opaque marker is a balloon catheter.

* * * * *

UNITED STATES PATENT AND TRADEMARK OFFICE
CERTIFICATE OF CORRECTION

PATENT NO.   : 6,450,976 B2
DATED        : September 17, 2002
INVENTOR(S)  : Joseph R. Korotko It is certified that error appears in the above-identified patent and that said Letters Patent is hereby corrected as shown below:

Column 1,
Line 35, replace "the affected length" with -- the length --.

Column 6,
Line 52, replace "by" with -- on --.

Signed and Sealed this

Fifteenth Day of April, 2003

JAMES E. ROGAN
*Director of the United States Patent and Trademark Office*